United States Patent [19]

Takahashi et al.

[11] 4,242,303
[45] Dec. 30, 1980

[54] GAS DETECTING ELEMENT

[75] Inventors: Takashi Takahashi, Toyko; Masaki Katsura, Mitaka; Tadao Kaneda, Yokohama; Hideaki Hiraki; Masayuki Shiratori, both of Kawasaki, all of Japan

[73] Assignee: Tokyo Shibaura Denki Kabushiki Kaisha, Kawasaki, Japan

[21] Appl. No.: 33,251

[22] Filed: Apr. 25, 1979

[30] Foreign Application Priority Data

| May 2, 1978 | [JP] | Japan | 53-52361 |
| May 2, 1978 | [JP] | Japan | 53-52365 |
| May 2, 1978 | [JP] | Japan | 53-52371 |
| Aug. 31, 1978 | [JP] | Japan | 53-105565 |

[51] Int. Cl.$^3$ ............................................. G01N 27/12
[52] U.S. Cl. ........................... 422/98; 324/715 N; 338/34; 340/634; 23/232 E
[58] Field of Search .................. 340/633, 634; 422/94–98; 338/22 SD, 34; 324/71 SN; 252/437, 461

[56] References Cited

U.S. PATENT DOCUMENTS

| 3,387,038 | 6/1968 | Koch | 252/461 |
| 3,952,567 | 4/1976 | Shinagawa et al. | 338/34 X |
| 3,961,248 | 6/1976 | Kawamara | 324/71 SN |
| 3,999,947 | 12/1976 | Mihara et al. | 338/34 |
| 4,015,230 | 3/1977 | Nitta et al. | 338/35 |
| 4,099,922 | 7/1978 | Yasada et al. | 422/95 |
| 4,128,503 | 12/1978 | Yamauchi et al. | 252/437 |
| 4,138,365 | 2/1979 | Ogawa | 252/437 |
| 4,145,314 | 3/1979 | Fung et al. | 252/437 |

FOREIGN PATENT DOCUMENTS

| 47-38840 | 9/1972 | Japan | |
| 51-84291 | 7/1976 | Japan | 422/98 |

OTHER PUBLICATIONS

Seiyama et al., "Study on a Det. for Gaseous Components Using Semi-conductive Thin Films", Analy. Chem. 38 7(1966), pp. 1069–1073.
Shaver, P. J., Activated Tungsten Oxide Gas Detectors, Applied Physics Letters 11, Oct. (1967), pp. 255–257.

*Primary Examiner*—Michael S. Marcus
*Attorney, Agent, or Firm*—Oblon, Fisher, Spivak, McClelland & Maier

[57] ABSTRACT

A gas detecting element having a high gas selectivity which comprises an N-type metal oxide semiconductor, 0.005 to 8% by weight, based on the metal oxide, of at least one noble metal catalyst selected from the group consisting of platinum (Pt), palladium (Pd) and rhodium (Rh) and phosphorus 1.5 to 30 times as much as that of the noble metal or 0.05 to 30 times as much as that of palladium where palladium alone is used as the noble metal catalyst.

3 Claims, 43 Drawing Figures

GAS DETECTING ELEMENT

This invention relates to a gas detecting element exhibiting a high gas selectivity.

A change in surface resistivity is caused if a certain kind of gas is brought into contact with a metal oxide semiconductor surface. A gas detecting element utilizing this phenomenon is known to the art. For example, N-type metal oxide semiconductors such as ZnO, $SnO_2$ and $Fe_2O_3$ will exhibit a decreased surface resistance if a reducing gas is brought into contact therewith. On the other hand, the resistance is increased if an oxidative gas is allowed to contact such metal oxides. The relationship in respect of the change in resistance is reversed when it comes to p-type metal oxide semiconductors.

The reactivity of metal oxide semiconductors with a particular kind of gas, i.e., gas selectivity, is determined by the surface temperature, surface electron level structure, porosity, pore size, etc, of the semiconductors. In general, however, a gas detecting element formed of a metal oxide semiconductor alone is not satisfactory in sensitivity and gas selectivity. It has been proposed to add a catalyst such as platinum or palladium to the metal oxide semiconductor in order to increase the sensitivity and gas selectivity of the gas detecting element. In this case, the gas selectivity can be improved to some extent by suitably selecting the surface temperature of the gas detecting element. For example, a gas sensitive material obtained by adding platinum to a metal oxide semiconductor exhibits a high sensitivity to isobutane, and is low in reactivity with hydrogen gas and carbon monoxide gas. Where palladium is added in place of platinum, the resultant gas sensitive material exhibits a high sensitivity to each of isobutane, hydrogen and carbon monoxide. However, a metal oxide semiconductor to which is added platinum or palladium exhibits a high sensitivity to alcoholic gases, too, such as ethyl alcohol gas. It follows that the conventional gas detecting element prepared by adding platinum and/or palladium to a metal oxide semiconductor also senses alcoholic gases generated from foods, hair conditioners, cosmetics, etc. as well as to liquefied petroleum gas (Lp gas). Naturally, the sensitivity to such alcoholic gases is undesirable particularly where the gas detecting element is used at home for detecting the leakage of Lp gas.

This invention is intended to overcome the above-noted difficulty and provides a gas detecting element highly sensitive to isobutane but scarcely sensitive to alcoholic gases. The element provided by this invention is particularly suitable for detecting the leakage of Lp gas widely used as domestic fuel.

According to this invention, there is provided a gas detecting element comprising a hollow cylindrical insulative body, a pair of electrodes provided on the outer circumference of said insulative body and a gas sensitive material layer covering up the outer periphery of said insulative body and said electrodes, wherein the gas sensitive material layer comprises an N-type metal oxide semiconductor, 0.005 to 8%, preferably 0.5 to 3%, by weight based on the metal oxide of at least one noble metal catalyst selected from the group consisting of platinum, palladium and rhodium, and phosphorus 1.5 to 30 times, preferably 1.5 to 15 times, in mol ratio as much as that of the noble metal or 0.05 to 30 times, preferably 0.05 to 15 times, in mol ratio as much as that of palladium where palladium alone is used as the noble metal catalyst. Particularly, it is preferred to use ZnO series materials, $SnO_2$ series materials or $Fe_2O_3$ series materials as the N-type metal oxide semiconductor. The gas detecting element of this construction is particularly advantageous in stability over a long period of use of the element as well as in sensitivity and gas selectivity.

This invention can be more fully understood from the following detailed description when taken in conjunction with the accompanying drawings, in which.

In this invention, it is possible to use known N-type metal oxide semiconductors. Particularly suitable for this invention are ZnO-based materials, $SnO_2$-based materials and $Fe_2O_3$-based materials including, for example, $ZnO\text{-}Cr_2O_3$, $ZnO\text{-}Al_2O_3$, $ZnO\text{-}Ga_2O_3$, $ZnO\text{-}Cr_2O_3\text{-}Al_2O_3$, $ZnO\text{-}Cr_2O_3\text{-}Ga_2O_3$, $ZnO\text{-}Al_2O_3\text{-}Ga_2O_3$, $ZnO\text{-}Cr_2O_3\text{-}Al_2O_3\text{-}Ga_2O_3$, $SnO_2\text{-}SiO_2$, $SnO_2\text{-}Sb_2O_3$, $SnO_2\text{-}SiO_2\text{-}Sb_2O_3$ and $Fe_2O_3\text{-}Al_2O_3$. Further, carriers such as alumina and silica can be used for supporting the noble metal catalyst and phosphorus in forming a catalyst layer on the surface of a gas sensitive material layer.

As described previously, 0.005 to 8% by weight of a noble metal catalyst selected from platinum, palladium and rhodium is added in this invention to the N-type metal oxide semiconductor. If the amount of the noble metal catalyst is smaller than 0.005 % by weight, the resultant gas sensitive element fails to exhibit a sufficiently high sensitivity to isobutane. On the other hand, the noble metal catalyst exceeding 8% by weight causes the produced element to exhibit an appreciably high sensitivity to alcoholic gases, too.

The amount of phosphorus used in this invention should be 1.5 to 30 times as much as that of the noble metal catalyst in mol ratio, though it is possible to set the lower limit of the phosphorus amount at 0.05 time as much as that of palladium if palladium alone is used as the noble metal catalyst. Where the amount of phosphorus is smaller than the lower limit mentioned above, the resultant gas detecting element is caused to exhibit sensitivity to both isobutane and alcoholic gases. In addition, the sensitivity to isobutane is not sufficiently high. An insufficient sensitivity to isobutane is also caused where the amount of phosphorus is more than 30 times in mol ratio as much as that of the noble metal catalyst.

It is possible in this invention to add the noble metal catalyst of platinum, palladium and rhodium to the N-type metal oxide semiconductor as elemental metal or in the form of an intermetallic compound thereof.

To be brief, this invention is featured in that predetermined amounts of a noble metal catalyst and phosphorus are added to an N-type metal oxide semiconductor so as to provide a gas detecting element highly sensitive to isobutane and scarcely sensitive to alcoholic gases. Naturally the element thus provided is suitable for detecting the leakage of LP gas. Also a catalyst layer containing predetermined amounts of the noble metal catalyst and phosphorus may be formed on the surface of an N-type metal oxide semiconductor layer so as to provide a gas detecting element. In this case, the resultant element is enabled to exhibit an improved stability over a long period of use in addition to the improved sensitivity and gas selectivity.

Figure 1:
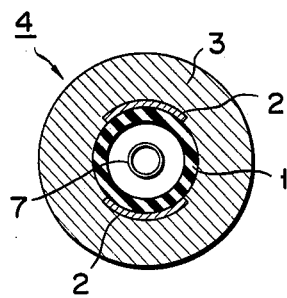
FIG. 1 is a cross sectional view showing the construction of a gas detecting element according to one embodiment of this invention.
Figure 2:
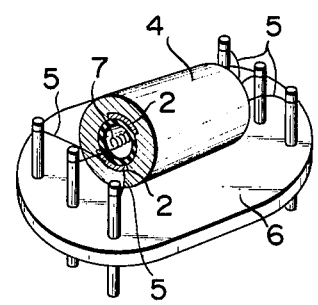
FIG. 2 is an oblique view showing an apparatus to which is mounted a gas detecting element of this invention.

Accompanying FIG. 1 shows a gas detecting element 4 according to one embodiment of this invention. It is seen that the element 4 comprises a cylindrical insulative substrate 1, a pair of electrodes 2 mounted to the outer circumference of the substrate 1, and a gas sensitive material layer 3 formed in a manner to cover both the substrate 1 and the electrode 2. The gas sensitive material mentioned is prepared by mixing predetermined amounts of a noble metal catalyst and phosphorus with an N-type metal oxide semiconductor. The gas sensitive element 4 of this construction is assembled as shown in FIG. 2. Reference numerals 5, 6 and 7 shown in FIG. 2 denote lead wires, an insulation plate and a heater, respectively. Incidentally, it is not absolutely necessary to provide the heater 7, which is intended to enhance the sensitivity of the gas sensitive material.

Figure 3:
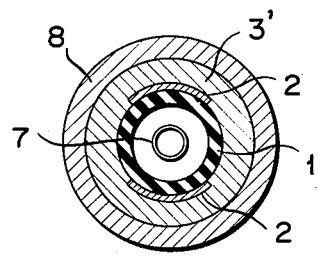
FIGS. 3 and 4 are cross sectional views showing the construction of a gas detecting element according to other embodiments of this invention.
Figure 4:
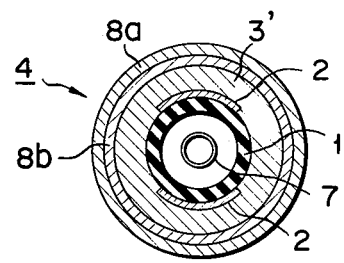
Figure 5:
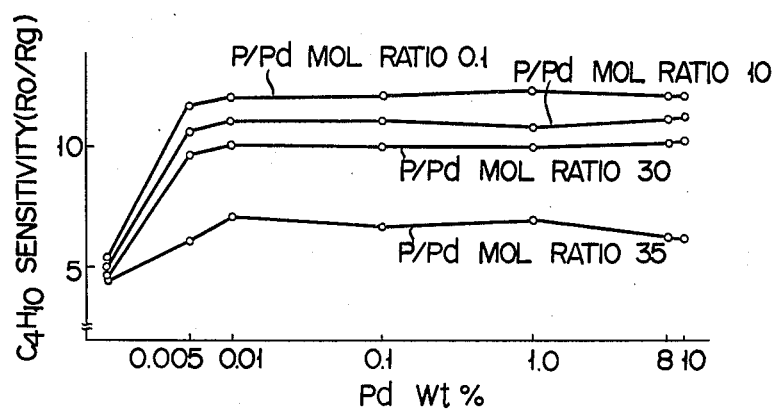
FIGS. 5 to 22 show the sensitivity of the gas detecting element according to this invention constructed as shown in FIG. 1.
Figure 6:
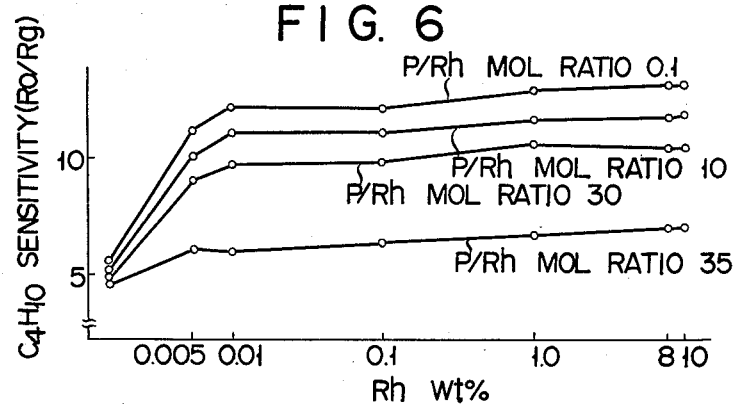
Figure 7:
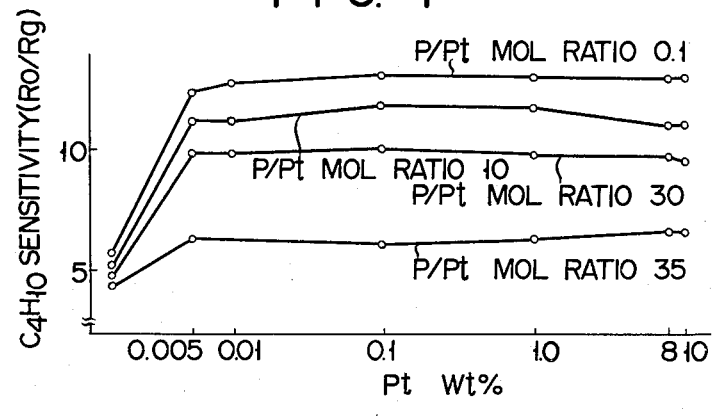
Figure 8:
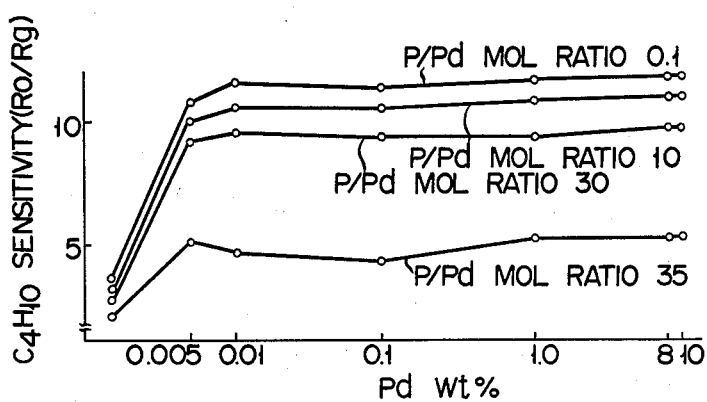
Figure 9:
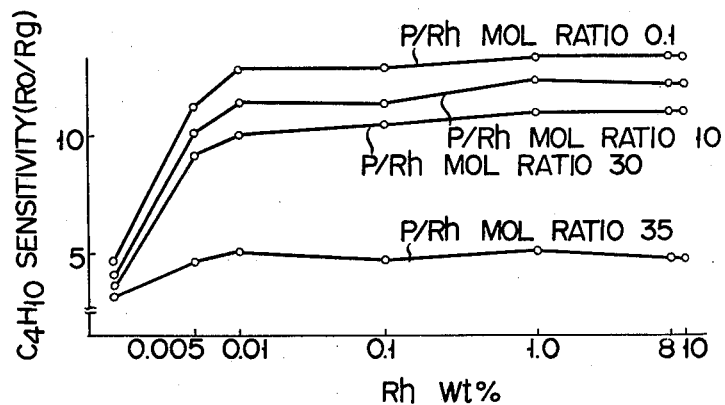
Figure 10:
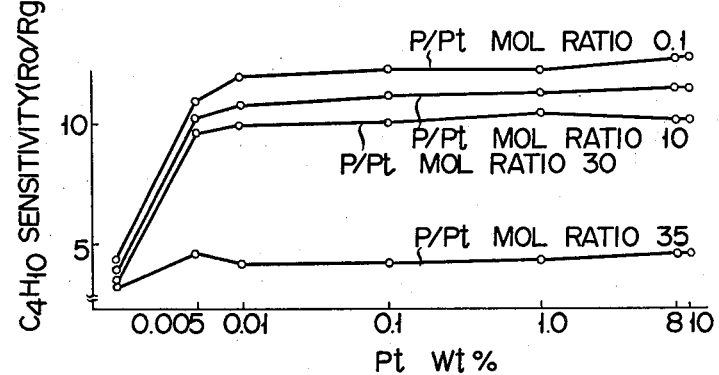
Figure 11:
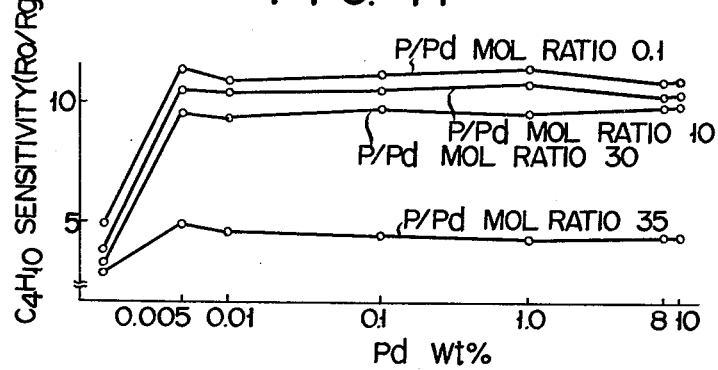
Figure 12:
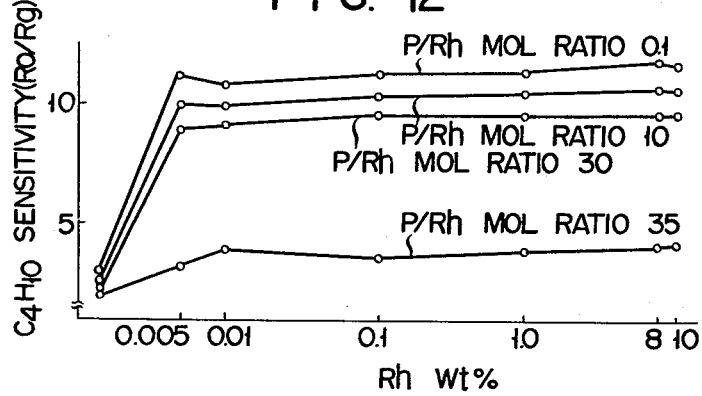
Figure 13:
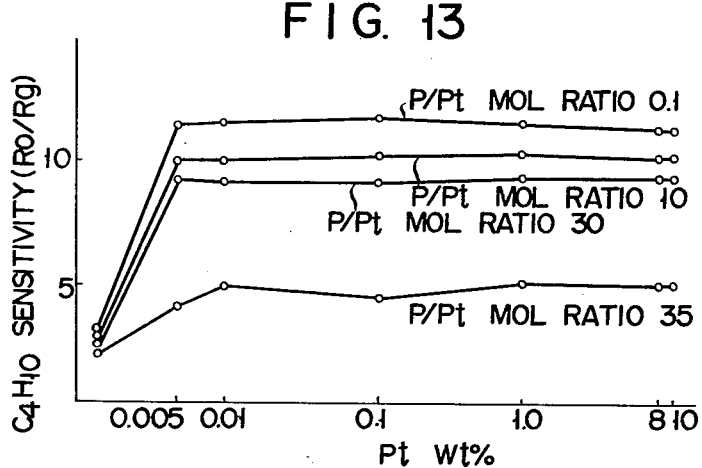
Figure 14:
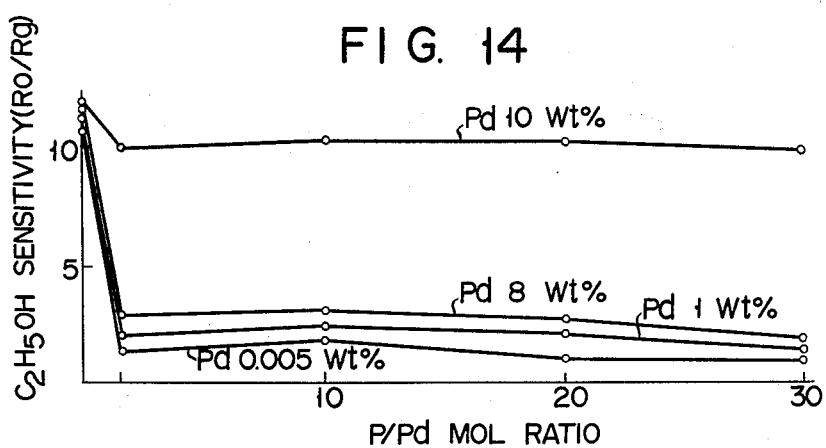
Figure 15:
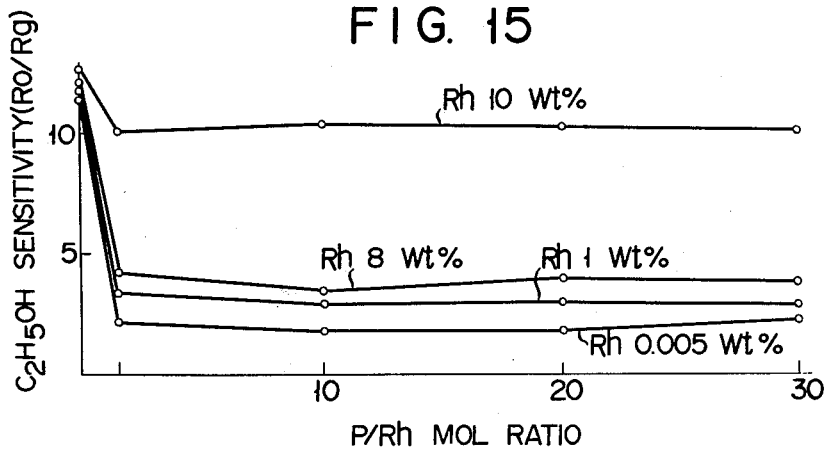
Figure 16:
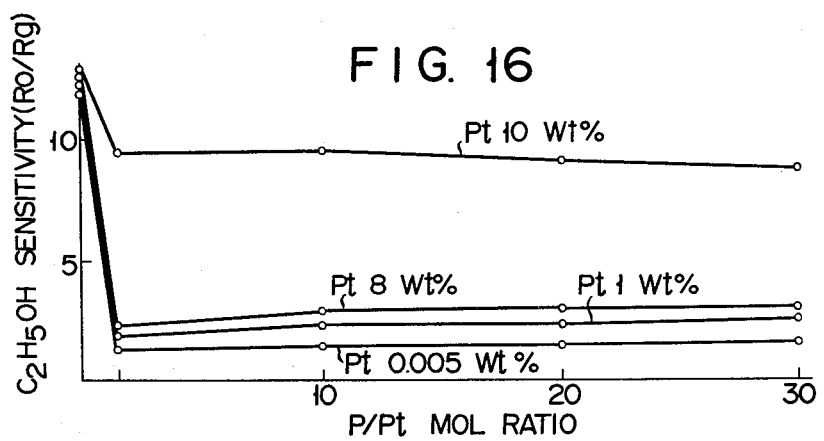
Figure 17:
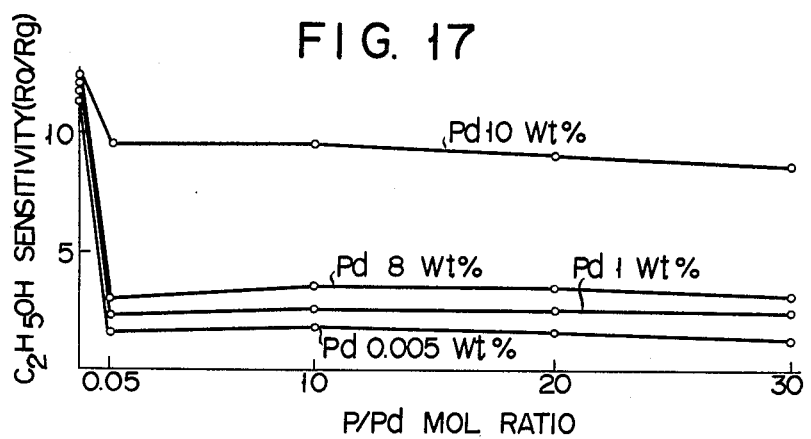
Figure 18:
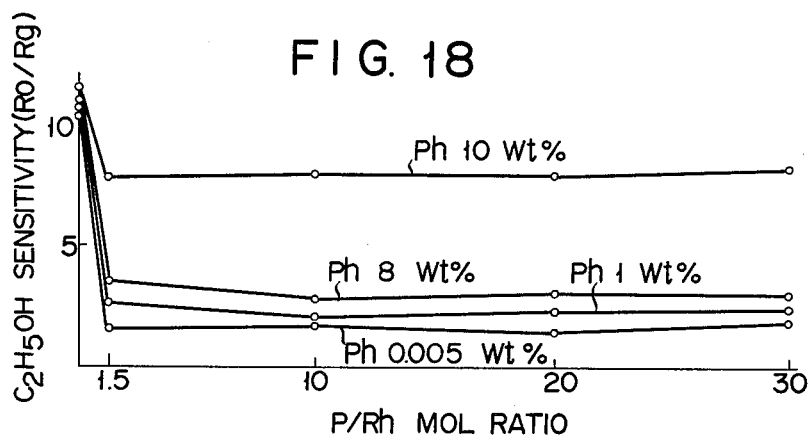
Figure 19:
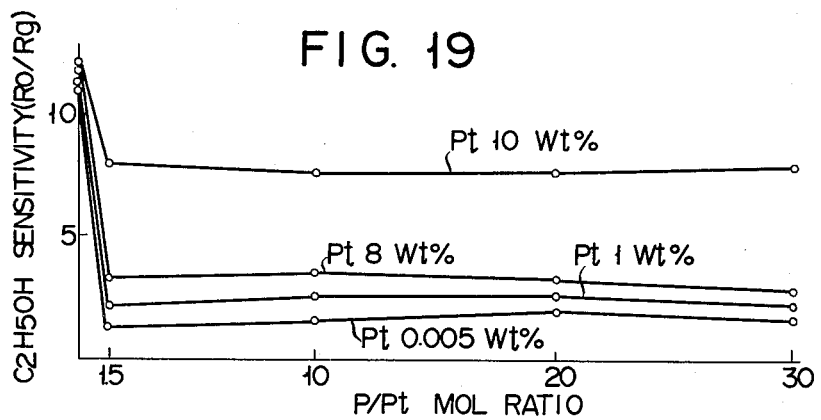
Figure 20:
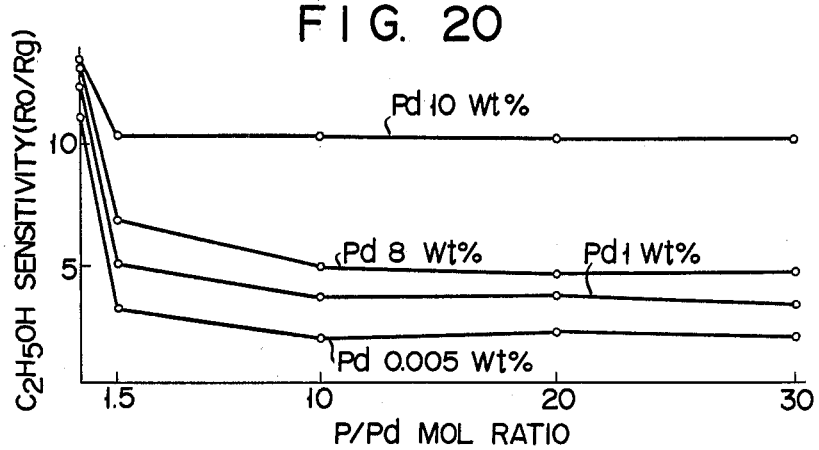
Figure 21:
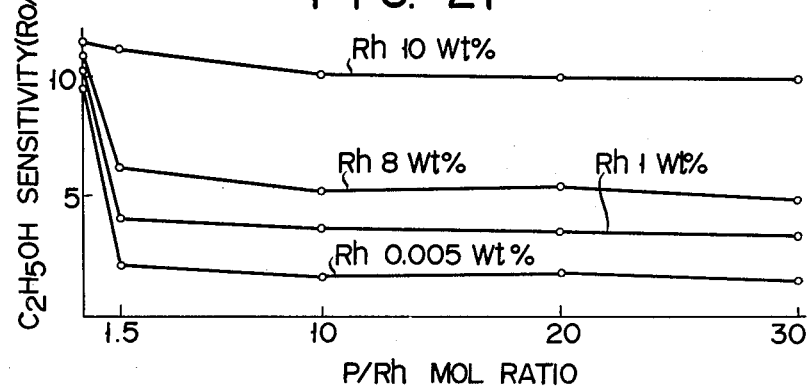
Figure 22:
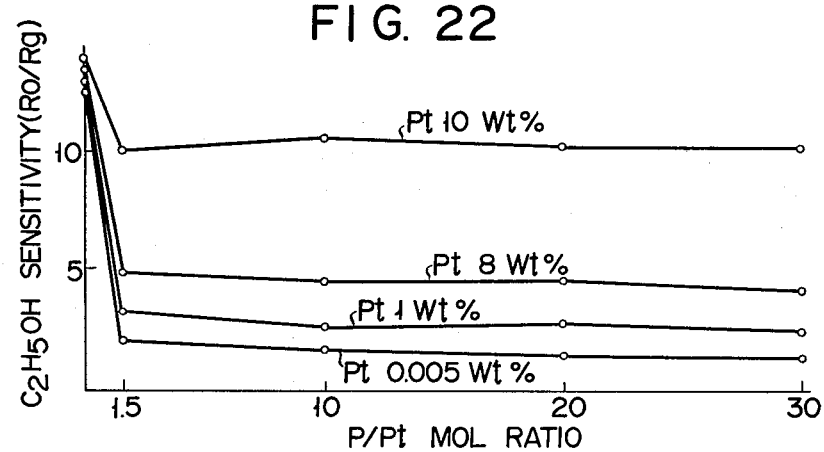
Figure 23:
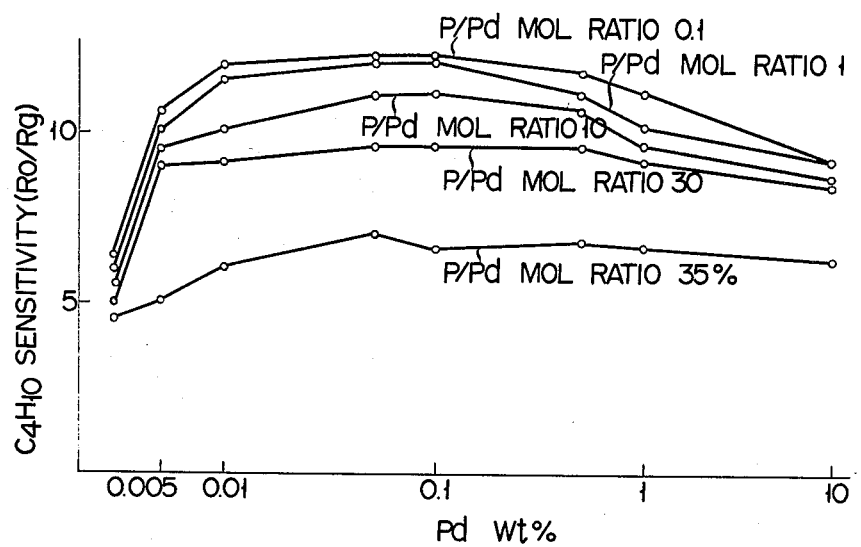
FIGS. 23 to 40 show the sensitivity of the gas detecting element according to this invention constructed as shown in FIG. 3.
Figure 24:
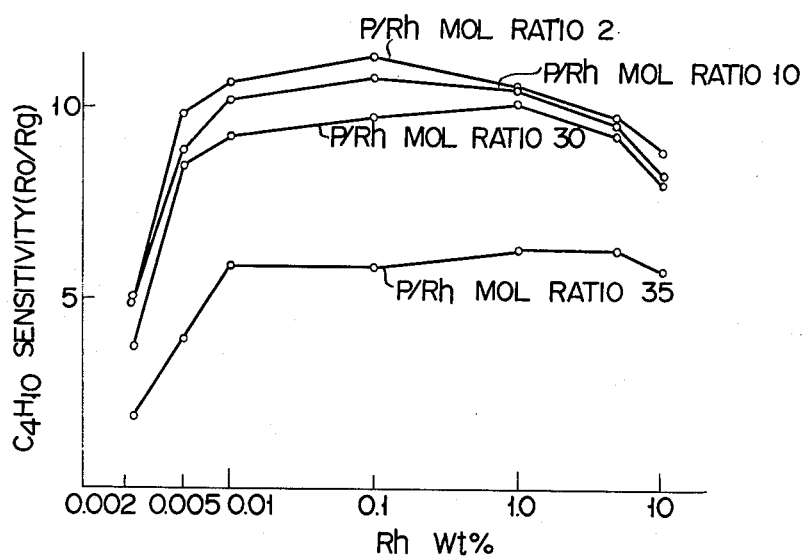
Figure 25:
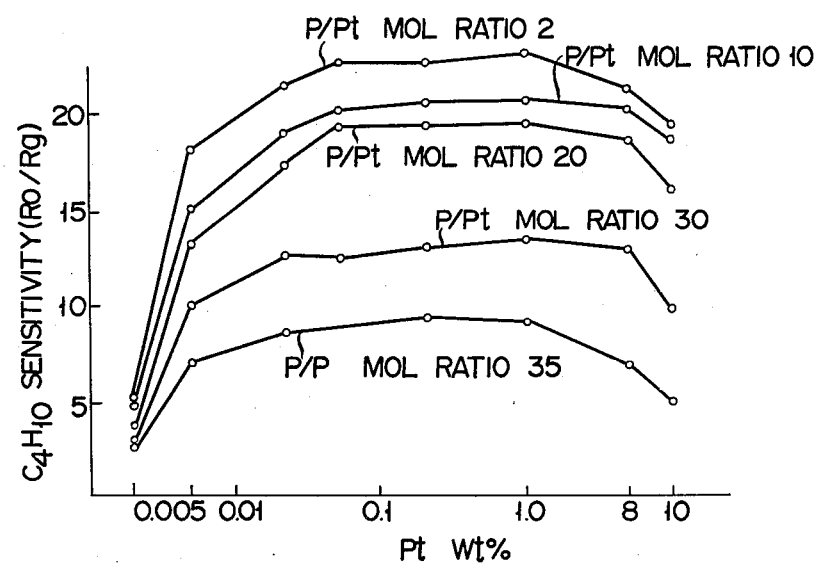
Figure 26:
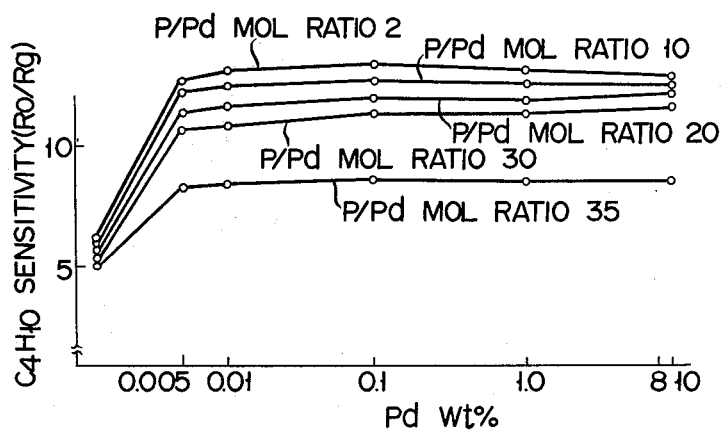
Figure 27:
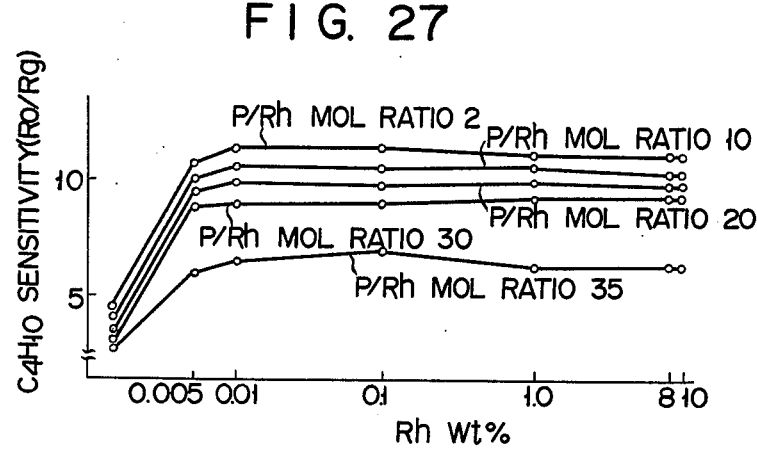
Figure 28:
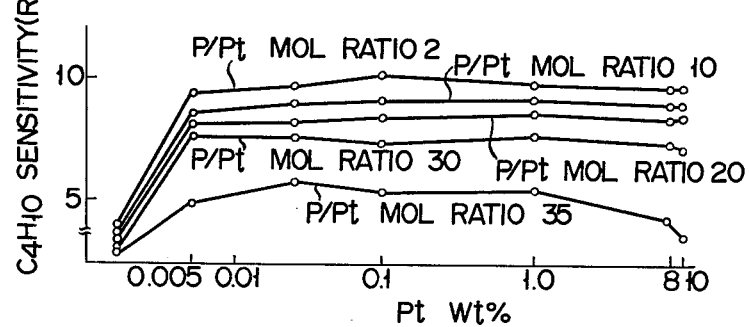
Figure 29:
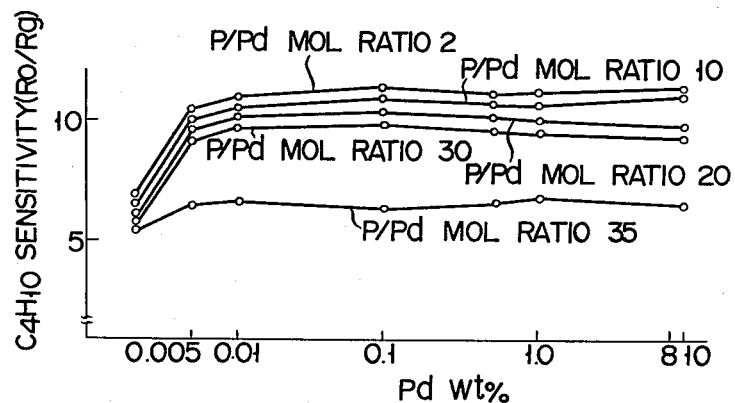
Figure 30:
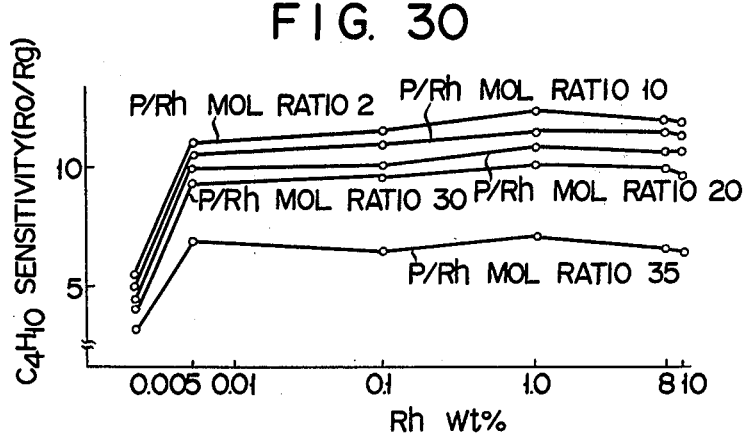
Figure 31:
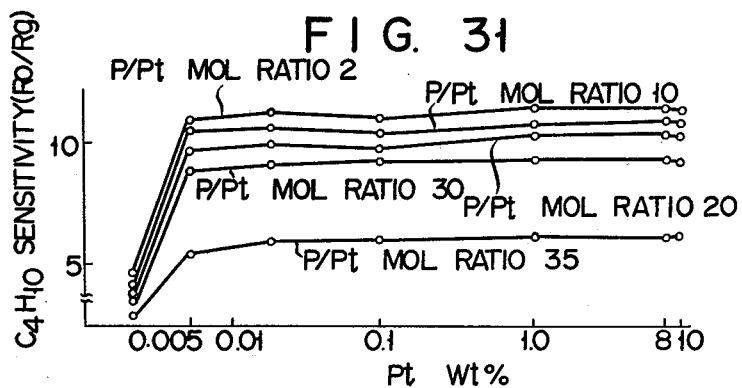
Figure 34:
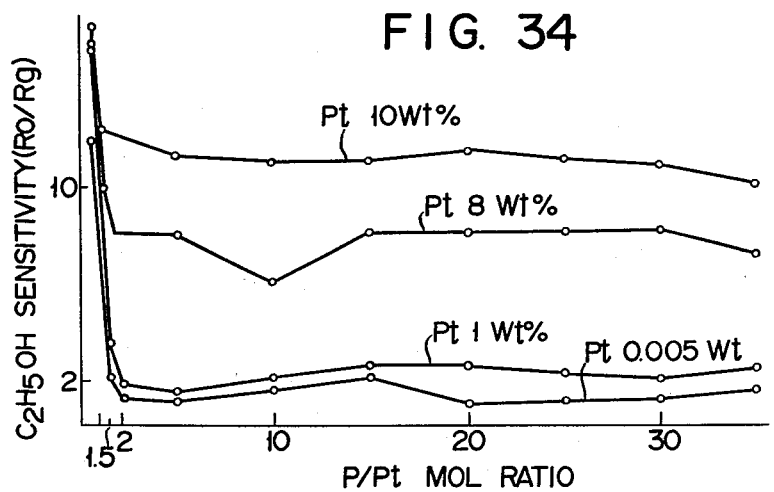
Figure 32:
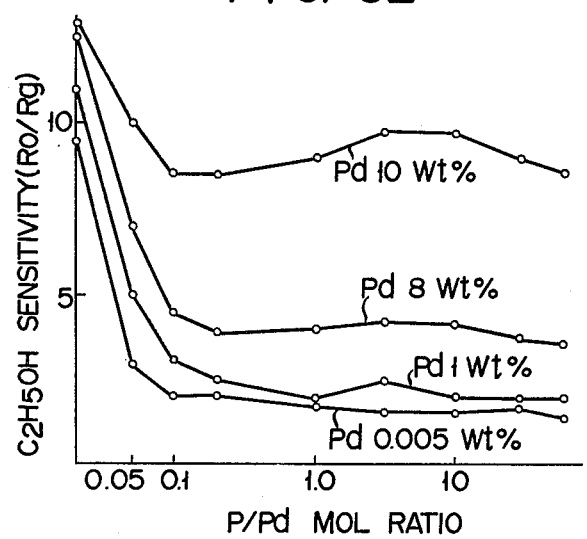
Figure 33:
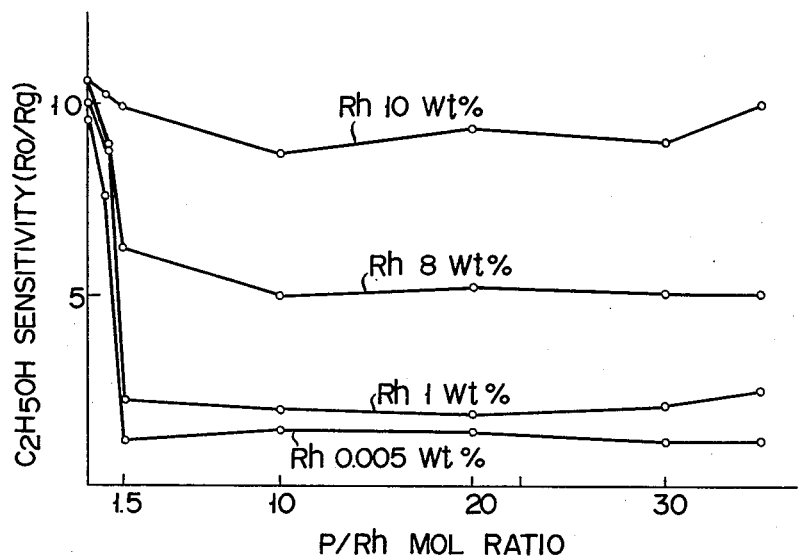
Figure 35:
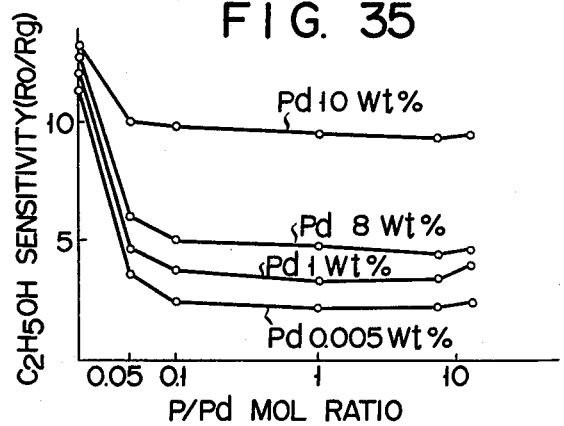
Figure 36:
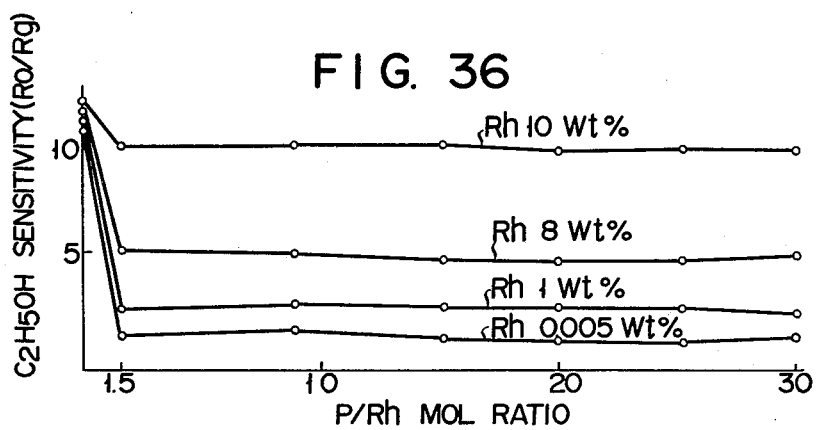
Figure 37:
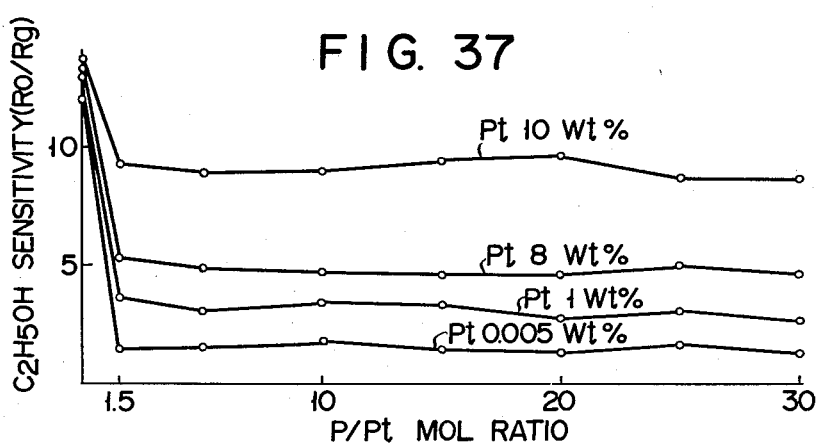
Figure 38:
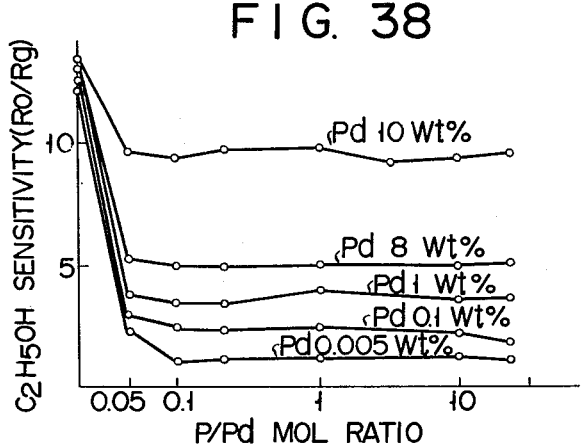
Figure 39:
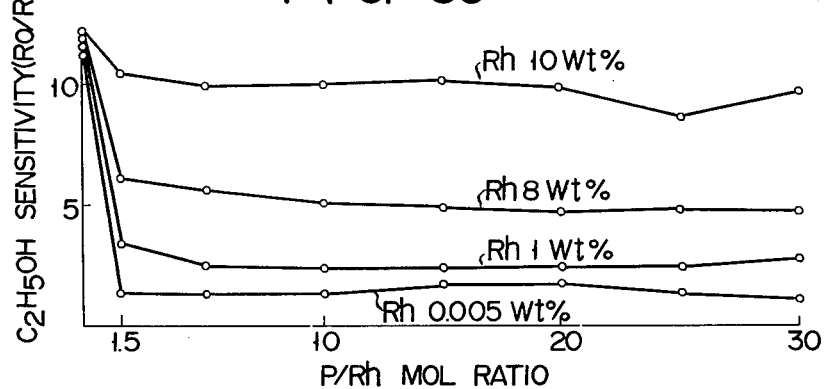
Figure 40:
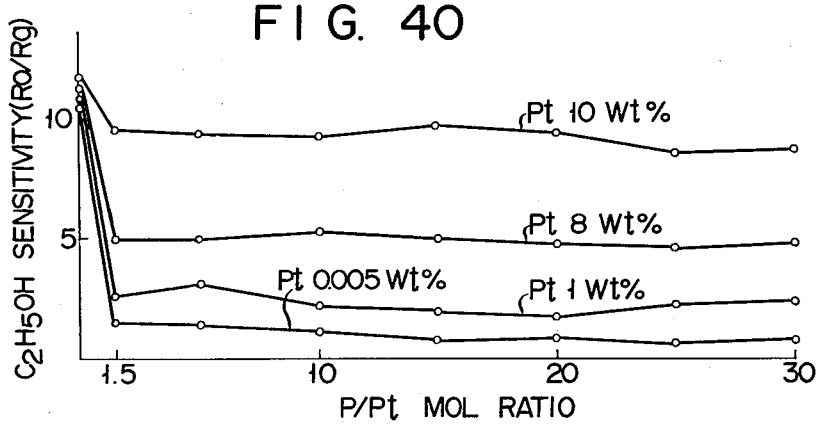

FIG. 3 shows another embodiment of this invention. In this case, a gas sensitive material layer 3' is formed of an N-type metal oxide semiconductor alone and a catalyst layer 8 containing predetermined amounts of a noble metal catalyst and phosphorus is formed on the outer surface of the layer 3'. Two more catalyst layers 8a, 8b made of different materials may be coated on the gas detecting body 3' as shown in FIG. 4, depending on the kinds of gases for which the gas detecting element 4 is to detect. Incidentally, it is possible to use carriers such as silica, alumina, zirconia, silica-alumina-based compounds and a composite material of these oxides for supporting the noble metal catalyst and phosphorus.

For producing the gas detecting element of FIG. 1, a predetermined amount of an N-type metal oxide semiconductor material is sufficiently mixed first with water or another suitable binder. To the resultant mixture is added a noble metal catalyst in the form of a solution of, for example, $H_2PtCl_2.6H_2O$; $RhCl_3.3H_2O$; $PdCl_2$ or $Pd(NO_3)_2$ together with phosphorus in the form of an inorganic phosphorus compound such as $H_3PO_4$ or $NH_4H_2PO_4$ so as to obtain a pasty gas sensitive material having a suitable pH value and a suitable viscosity. The pasty material thus prepared is coated on the cylindrical insulative substrate 1 equipped with the electrodes 2, followed by drying and, subsequently, baking at 300° to 1,100° C. so as to obtain the gas sensitive element 4.

When it comes to the element shown in FIG. 3, a pasty material prepared by adding water or another suitable binder to a predetermined amount of an N-type metal oxide semiconductor material is coated on the cylindrical insulative substrate 1 equipped with the electrodes 2 followed by drying and, subsequently, baking at 300° to 1,100° C. so as to form the gas sensitive material layer 3'. Unlike the element 4 of FIG. 1, the element of FIG. 3 comprises the catalyst layer 8 which is prepared separately. For preparation of the catalyst layer 8, a mixture containing a noble metal catalyst in the form of a solution of, for example, $H_2PtCl_2.6H_2O$; $RhCl_3.3H_2O$; $PdCl_2$ or $Pd(NO_3)_2$, phosphorus in the form of $H_3PO_4$, $NH_4H_2PO_4$, etc., and suitable silica alumina-based compounds, if necessary, as the carrier of the catalyst and phosphorus is fully mixed so as to obtain a slurry or paste having a suitable pH value and a suitable viscosity. After fully mixed, the slurry or paste is dried and, then, baked at 300° to 1,100° C., followed by grinding the baked mass so as to obtain fine powder. The resultant powder is mixed with water or another suitable binder so as to obtain a pasty material. Finally, the pasty material is coated on the gas sensitive material layer 3' formed in advance, followed by drying and, subsequently, baking at 300° to 1,000° C., thereby obtaining the gas detecting element having the catalyst layer 8 formed on the gas sensitive material layer 3'.

The gas detecting element according to this invention exhibits a prominently high sensitivity to LP gas and a sufficiently low sensitivity to an alcoholic gas as seen from FIGS. 4 to 38. Through these Figures, the sensitivity of the gas detecting element is represented by the ratio of Ro/Rg in which Ro denotes the resistance of the element disposed under the air atmosphere with Rg denoting the resistance of the element disposed under the atmosphere containing 0.2% by volume of isobutane or ethyl alcohol.

Specifically, FIGS. 4 to 21, which are concerned with the element constructed as shown in FIG. 1, show the relationship between the amounts of the noble metal catalyst and phosphorus and the sensitivity of the element to isobutane or ethyl alcohol. It is seen that FIGS. 4 to 12 show the sensitivity of the element to isobutane, with FIGS. 13 to 21 showing the sensitivity of the element to ethyl alcohol. It should be noted that FIGS. 4 to 6 and 13 to 15 cover the cases where $ZnO-Cr_2O_3$ was used as the N-type metal oxide semiconductor included in the gas detecting element. Likewise, FIGS. 7 to 9 and 16 to 18 cover the cases of using $SnO_2-SiO_2$ as the N-type metal oxide semiconductor, with FIGS. 10 to 12 and 19 to 21 covering the cases of using $Fe_2O_3-Al_2O_3$ as the N-type metal oxide semiconductor.

It is clearly seen that the gas detecting element exhibits a high sensitivity to isobutane where the amount of the noble metal catalyst such as platinum, palladium or rhodium is not smaller than 0.005% by weight and, at the same time, the ratio of phosphorus to the noble metal catalyst is not larger than 30 in mol ratio. On the other hand the gas detecting element exhibits a high sensitivity to ethyl alcohol, too, as well as to isobutane where the amount of the noble metal catalyst is larger than 8% by weight based on the metal oxide and the ratio of phosphorus to the noble metal mentioned above is smaller than 1.5. In this case, the gas detecting element can not be put to actual uses because the element exhibits a high sensitivity to alcoholic gases, too. For the case of using palladium alone as the noble metal catalyst, the difficulty mentioned above is encountered where the ratio of phosphorus to palladium is smaller than 0.05 in mol ratio.

Additional experiments were conducted by using gas detecting elements constructed as shown in FIG. 1 and containing $ZnO-Cr_2O_3$ as the N-type metal oxide semiconductor. In these experiments, hydrogen gas and carbon monoxide gas were also used as the gases to be detected. Table 1 shows the results of the experiments together with Control cases.

TABLE 1

| | Catalyst | Detected Gas [0.2 vol %] | | | |
|---|---|---|---|---|---|
| | | $H_2$ | CO | $C_4H_{10}$ | $C_2H_5OH$ |
| Example -1 | Pt—P | 2.0 | 1.7 | 12.0 | 3.1 |
| -2 | Pd—P | 12.0 | 4.1 | 10.9 | 2.5 |
| -3 | Rh—P | 3.8 | 1.9 | 10.5 | 1.7 |
| -4 | Pt—Pd—P | 8.0 | 1.4 | 10.5 | 2.1 |
| -5 | Pd—Rh—P | 10.7 | 3.9 | 10.2 | 2.2 |
| -6 | Rh—Pt—P | 3.1 | 1.7 | 11.0 | 2.8 |
| -7 | Pt—Pd—Rh—P | 7.2 | 1.5 | 11.3 | 2.5 |
| Control -1 | | 4.4 | 3.0 | 5.1 | 5.9 |
| -2 | P | 3.8 | 1.6 | 1.9 | 4.4 |
| -3 | Pt | 2.1 | 1.9 | 12.5 | 12.5 |
| -4 | Pd | 12.8 | 3.0 | 11.0 | 11.8 |
| -5 | Rh | 7.6 | 1.5 | 12.1 | 10.3 |
| -6 | Pt—Pd | 8.4 | 2.6 | 11.7 | 12.0 |
| -7 | Pd—Rh | 11.2 | 4.3 | 11.9 | 10.8 |
| -8 | Rh—Pt | 4.3 | 1.9 | 12.0 | 11.4 |
| -9 | Pt—Pd—Rh | 7.7 | 1.5 | 12.0 | 11.4 |

Table 1 clearly shows that the gas detecting element according to this invention exhibits a high gas selectivity. Specifically, the sensitivities of the element to ethyl alcohol and isobutane were very low and very high, respectively. In contrast, the element which did not contain a catalyst was low in sensitivities to both ethyl alcohol and isobutane. Further, the sensitivity to ethyl alcohol was higher than that to isobutane. Further, where phosphorus alone or the noble metal catalyst alone was used as the catalytic material, the element exhibited a high sensitivity to ethyl alcohol, too, as well as to isobutane.

Still additional experiments were conducted by using gas detecting elements constructed as shown in FIG. 1 and containing $SnO_2$-$SiO_2$ or $Fe_2O_3$-$Al_2O_3$ as the N-type noble metal semiconductor. Tables 2 and 3 show the results of the experiments together with Control cases. Incidentally, Tables 2 and 3 cover the cases of using $SnO_2$-$SiO_2$ and $Fe_2O_3$-$Al_2O_3$ as the N-type metal oxide semiconductors, respectively.

TABLE 2

| | Catalyst | Detected Gas [0.2 vol %] | | | |
|---|---|---|---|---|---|
| | | $H_2$ | CO | $C_4H_{10}$ | $C_2H_5OH$ |
| Example -8 | Pt—P | 1.9 | 1.8 | 12.0 | 2.0 |
| -9 | Pd—P | 10.0 | 1.8 | 10.4 | 2.8 |
| -10 | Rh—P | 1.9 | 1.6 | 12.5 | 2.0 |
| -11 | Pt—Pd—P | 6.8 | 1.2 | 10.0 | 2.1 |
| -12 | Pd—Rh—P | 7.6 | 1.8 | 10.3 | 2.4 |
| -13 | Rh—Pt—P | 1.7 | 1.8 | 11.8 | 1.9 |
| -14 | Pt—Pd—Rh—P | 7.4 | 2.1 | 11.1 | 2.9 |
| Control-10 | | 6.2 | 4.1 | 3.0 | 9.6 |
| -11 | P | 4.3 | 3.5 | 3.8 | 4.0 |
| -12 | Pt | 2.0 | 2.0 | 12.2 | 12.0 |
| -13 | Pd | 10.6 | 2.3 | 4.5 | 11.0 |
| -14 | Rh | 2.5 | 2.4 | 12.2 | 10.9 |
| -15 | Pt—Pd | 6.9 | 1.4 | 9.8 | 10.0 |
| -16 | Pd—Rh | 8.1 | 2.6 | 10.4 | 10.7 |
| -17 | Rh—Pt | 2.1 | 1.9 | 12.0 | 11.0 |
| -18 | Pt—Pd—Rh | 7.6 | 1.8 | 11.1 | 11.7 |

TABLE 3

| | Catalyst | Detected Gas [0.2 vol %] | | | |
|---|---|---|---|---|---|
| | | $H_2$ | CO | $C_4H_{10}$ | $C_2H_5OH$ |
| Example -15 | Pt—P | 2.0 | 1.7 | 12.0 | 3.1 |
| -16 | Pd—P | 12.0 | 4.1 | 10.9 | 2.5 |
| -17 | Rh—P | 3.8 | 1.9 | 10.5 | 1.7 |
| -18 | Pt—Pd—P | 8.0 | 1.4 | 10.5 | 2.1 |
| -19 | Pt—Rh—P | 10.7 | 3.9 | 10.2 | 2.2 |
| -20 | Rh—Pt—P | 3.1 | 1.7 | 11.0 | 2.8 |
| -21 | Pt—Pd—Rh—P | 7.2 | 1.5 | 11.3 | 2.5 |
| Control-19 | | 4.4 | 3.0 | 5.1 | 5.9 |
| -20 | P | 3.8 | 1.6 | 1.9 | 4.4 |

TABLE 3-continued

| | Catalyst | Detected Gas [0.2 vol %] | | | |
|---|---|---|---|---|---|
| | | $H_2$ | CO | $C_4H_{10}$ | $C_2H_5OH$ |
| -21 | Pt | 2.1 | 1.9 | 12.5 | 12.5 |
| -22 | Pd | 12.8 | 3.0 | 11.0 | 11.8 |
| -23 | Rh | 7.6 | 1.5 | 12.1 | 10.3 |
| -24 | Pt—Pd | 8.4 | 2.6 | 11.7 | 12.0 |
| -25 | Pd—Rh | 11.2 | 4.3 | 11.9 | 10.8 |
| -26 | Rh—Pt | 4.3 | 1.9 | 12.0 | 11.4 |
| -27 | Pt—Pd—Rh | 7.7 | 1.5 | 12.0 | 11.4 |

Tables 2 and 3 also show that the gas detecting element containing both the noble metal catalyst and phosphorus exhibits a high sensitivity to isobutane and a very low sensitivity to ethyl alcohol where $SnO_2$-based material or $Fe_2O_3$-based material is used as the N-type metal oxide semiconductor in stead of ZnO-based material.

FIGS. 22 to 39, which are concerned with the gas detecting element constructed as shown in FIG. 3, show the relationship between the amounts of the noble metal catalyst and phosphorus and the sensitivity of the element to isobutane or ethyl alcohol. It is seen that FIGS. 22 to 30 show the sensitivity of the elements to isobutane, with FIGS. 31 to 39 showing the sensitivity to ethyl alcohol. It should be noted that FIGS. 22 to 24 and 31 to 33 cover the cases where ZnO-$Cr_2O_3$ was used as the N-type metal oxide semiconductor included in the gas detecting element. Likewise, FIGS. 25 to 27 and 34 to 36 cover the cases of using $SnO_2$-$SiO_2$ as the N-type metal oxide semiconductor, with FIGS. 28 to 30 and 37 to 39 covering the cases of using $Fe_2O_3$-$Al_2O_3$ as the N-type metal oxide semiconductor.

It is seen from FIGS. 22 to 39 that the gas detecting element constructed as shown in FIG. 3 exhibits a high sensitivity to isobutane and a low sensitivity to an alcoholic gas where the catalyst layer contains 0.005 to 8% by weight, based on the metal oxide, of the noble metal catalyst and phosphorus in an amount of 1.5 to 30 times as much as that of the noble metal catalyst in mol ratio, as is the case with the element constructed as shown in FIG. 1. For the case of using palladium alone as the noble metal catalyst, the prominent effect of this invention is produced even where the amount of phosphorus ranges between 0.05 and 30 times as much as that of palladium in mol ratio. It is important to note that the element constructed as shown in FIG. 3 can be produced easily because the catalyst layer and the gas sensitive material layer are prepared separately for producing the gas sensitive element of thus particular construction. It should also be noted that the element as shown in FIG. 3 permits preventing the catalyst from being diffused into the gas sensitive material layer even where the element is used as a high temperature over a long period of time. In other words, the gas detecting element of this particular construction permits minimizing the deterioration with time in sensitivity and gas selectivity.

Additional experiments were conducted by using gas detecting elements constructed as shown in FIG. 3 and containing ZnO-$Cr_2O_3$, $SnO_2$-$SiO_2$ or $Fe_2O_3$-$Al_2O_3$ as the N-type metal oxide semiconductor. Table 4 shows the results of the experiments together with Control cases.

TABLE 4

| Gas Detecting Material | Catalyst | H₂ | CO | C₄H₁₀ | C₂H₅OH |
|---|---|---|---|---|---|
| Example-22 | | Pt—P | 1.2 | 1.1 | 22.0 | 1.7 |
| -23 | | Pd—P | 13.0 | 6.2 | 10.0 | 1.8 |
| -24 | ZnO—Cr₂O₃) | Rh—P | 4.0 | 1.9 | 10.9 | 2.0 |
| Control-28 | | | 4.4 | 3.1 | 5.0 | 6.0 |
| -29 | | P | 3.7 | 1.7 | 2.0 | 4.3 |
| -30 | | Pt | 2.4 | 1.1 | 10.3 | 12.6 |
| -31 | | Pd | 13.0 | 2.3 | 14.0 | 15.0 |
| -32 | | Rh | 8.0 | 1.4 | 12.0 | 10.0 |
| Example Pt—P | 2.3 | 3.1 | 10.0 | 2.7 | | |
| -26 | | Pd—P | 10.0 | 2.3 | 13.0 | 3.2 |
| -27 | (SnO₂—SiO₂) | Rh—P | 1.9 | 1.7 | 10.9 | 2.1 |
| Control-33 | | | 6.7 4.3 | 3.0 | 9.8 | |
| -34 | | P | 4.5 | 3.7 | 4.0 | 4.3 |
| -35 | | Pt | 1.9 | 2.0 | 13.0 | 13.3 |
| -36 | | Pd | 10.8 | 2.7 | 4.1 | 12.4 |
| -37 | | Rh | 2.3 | 2.1 | 12.2 | 11.5 |
| Example-28 | | Pt—P | 1.9 | 2.1 | 11.5 | 2.5 |
| -29 | | Pd—P | 12.9 | 4.3 | 13.0 | 2.5 |
| -30 | (Fe₂O₃— | Rh—P | 1.8 | 1.4 | 12.5 | 3.0 |
| Control-38 | Al₂O₃) | | 5.7 | 5.4 | 4.0 | 9.8 |
| -39 | | P | 4.1 | 3.2 | 4.4 | 6.3 |
| -40 | | Pt | 1.7 | 2.3 | 12.0 | 10.7 |
| -41 | | Pd | 11.0 | 2.6 | 14.0 | 14.6 |
| -42 | | Rh | 2.1 | 3.3 | 12.1 | 11.5 |

Table 4 shows that the gas detecting element of this invention constructed as shown in FIG. 3 exhibits a high gas selectivity, as is the case with the element of this invention constructed as shown in FIG. 1. Specifically, the element of this invention as shown in FIG. 3 exhibits a high sensitivity to isobutane and a sufficiently low sensitivity to ethyl alcohol. Incidentally, the life of the element constructed as shown in FIG. 3 was found to be more than 3 times as long as that of the element having a construction of FIG. 1 where the element was operated at, for example, 350° C.

Figure 41:
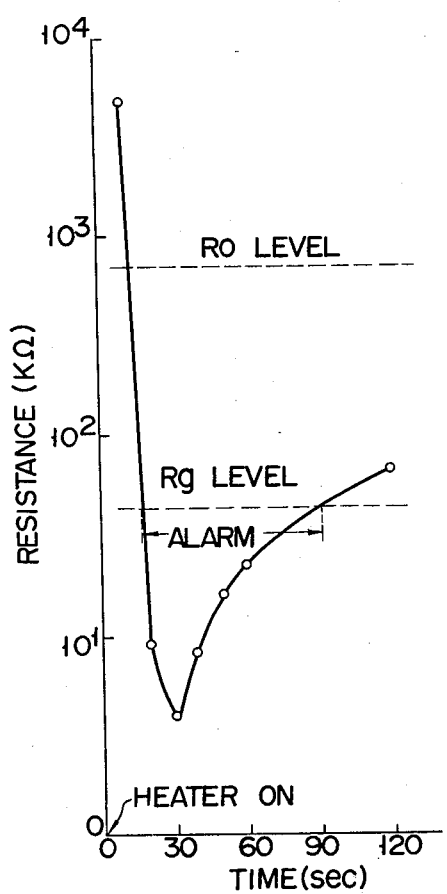
FIG. 41 shows a change in resistance with time of a gas detecting element according in the prior art.
Figure 42:
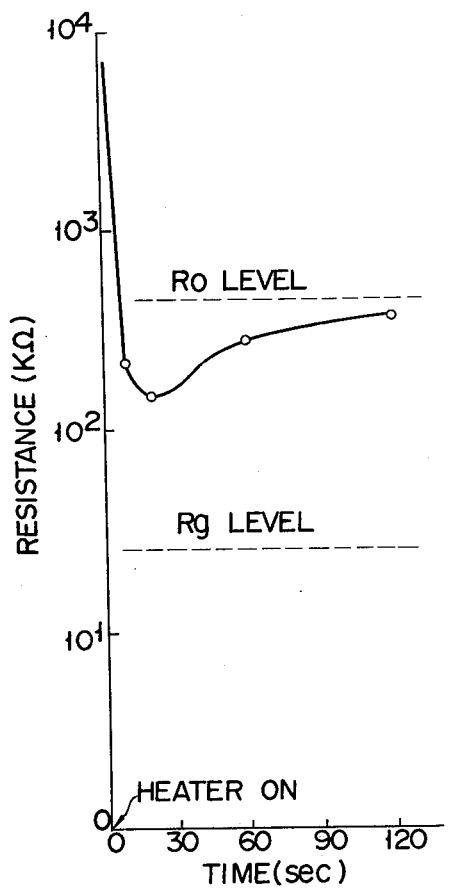
FIG. 42 shows a change in resistance with time of a gas detecting element according to this invention.

If a conventional gas detecting element is left unused for a long period of time, miscellaneous gases present in the atmosphere are adsorbed thereon, resulting in that, when electric power is supplied in using again the element, the element is caused to sound an alarm temporarily even in the absence of the gas to be detected. FIG. 41 is directed to a conventional gas detecting element formed of a ZnO-Sb₂O₃ semiconductor to which is added a platinum catalyst. It is clearly seen that the resistance of the element is held lower than the Rg level for scores of seconds after the heater of the element was turned on, resulting in sounding of an alarm. In contrast, FIG. 42 is concerned with a gas detecting element according to this invention in which is used a Rh-P catalyst, i.e., the element of Example 24. FIG. 42 clearly shows that the resistance reduction caused by the adsorption of miscellaneous gases is so small that the gas detecting element does not sound an alarm at the initial stage of restart-up of the element. In addition, the resistance of the element is rapidly brough to the Ro level, i.e., the resistance exhibited by the element when disposed under the open air atmosphere.

Figure 43:
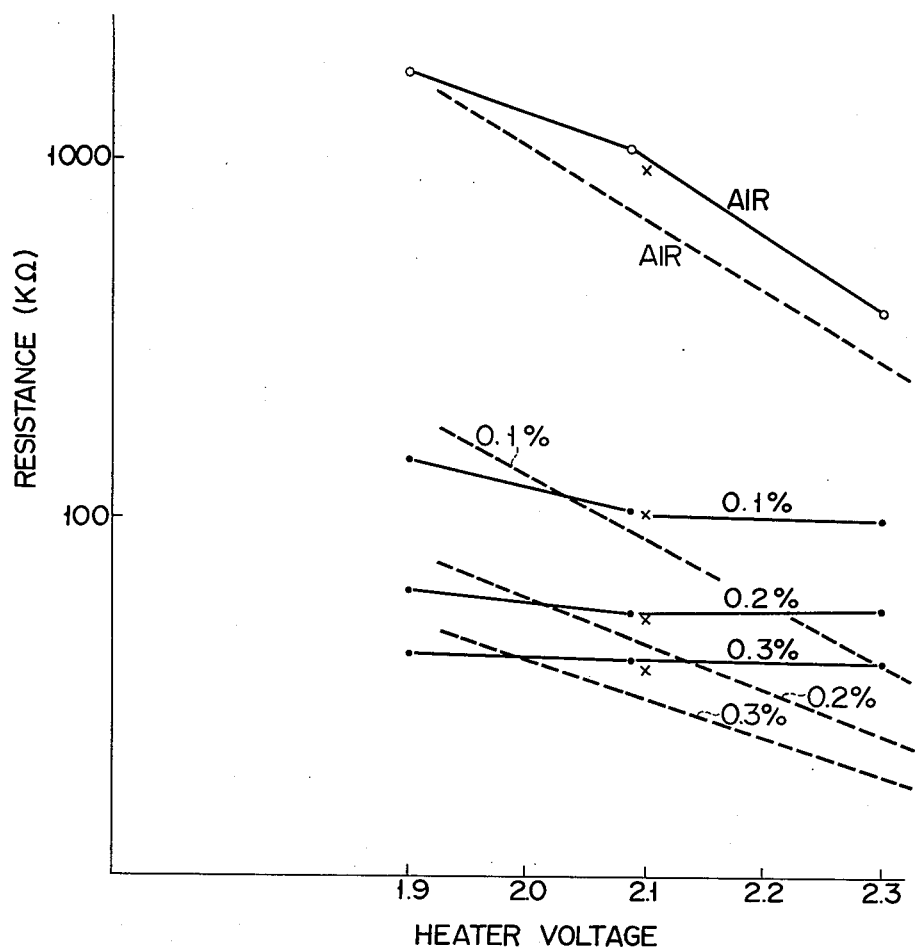
FIG. 43 shows dependability on heater voltage of a gas detecting element of this invention in comparison with that of the prior art.

It is also important to note that the gas detecting element of this invention is very low in dependency of the resistance on the heater voltage. Specifically, FIG. 43 shows the relationship between the resistance of the gas detecting element and the heater voltage. In the drawing, the dotted lines represent a conventional gas detecting element formed of a ZnO-Sb₂O₃ semiconductor to which is added a platinum catalyst, with the solid lines donoting the element of this invention comprising a Rh-P catalyst, i.e., the element of Example 24. FIG. 43 clearly shows that the resistance level in the gas of the element of this invention is substantially constant regardless of the change in heater voltage particularly where an appreciable amount of LP gas is contained in the atmosphere, rendering it unnecessary to provide a heater voltage stabilizing circuit.

As described in detail, the gas detecting element of this invention exhibits a high sensitivity to isobutane and a very low sensitivity to an alcoholic gas. It follows that the element of this invention is very suitable for use at home for detecting the leakage of LP gas.

What we claim is:

1. A gas detecting element comprising a hollow cylindrical insulative body, a pair of electrodes provided on the outer circumference of said insulative body and a gas sensitive material layer covering up the outer periphery of said insulative body and said electrodes, wherein the gas sensitive material layer comprises:
   an N-type metal oxide semiconductor;
   0.005 to 8% by weight, based on the metal oxide, of at least one noble metal catalyst selected from the group consisting of platinum (Pt), palladium (Pd) and rhodium (Rh); and
   phosphorus in an amount of 1.5 to 30 times in mol ratio as much as that of the noble metal or 0.05 to 30 times in mol ratio as much as that of palladium where palladium alone is used as the noble metal catalyst.

2. The gas detecting element according to claim 1, wherein the catalyst layer is formed on the surface of the N-type metal oxide semiconductor.

3. The gas detecting element according to claim 1, or wherein the N-type metal oxide semiconductor is provided by zinc oxide (ZnO) series materials, tin oxide (SnO₂) series materials or iron oxide (Fe₂O₃) series materials.

* * * * *